United States Patent
Pipal et al.

(10) Patent No.: US 10,072,012 B2
(45) Date of Patent: Sep. 11, 2018

(54) PROCESS FOR CRYSTALLINE PEMETREXED DIPOTASSIUM SALT

(71) Applicant: SHILPA MEDICARE LIMITED, Karnataka (IN)

(72) Inventors: Bhagat Raj Pipal, Raichur (IN); Venkata Reddy Gayam, Raichur (IN); Akshay Kant Chaturvedi, Raichur (IN)

(73) Assignee: Shilpa Mecicare Limited (IN)

( * ) Notice: Subject to any disclaimer, the term of this patent is extended or adjusted under 35 U.S.C. 154(b) by 29 days.

(21) Appl. No.: 15/036,819

(22) PCT Filed: Nov. 11, 2014

(86) PCT No.: PCT/IB2014/065954
§ 371 (c)(1),
(2) Date: May 16, 2016

(87) PCT Pub. No.: WO2015/075601
PCT Pub. Date: May 28, 2015

(65) Prior Publication Data
US 2016/0280710 A1  Sep. 29, 2016

(30) Foreign Application Priority Data
Nov. 25, 2013 (IN) .......................... 5404/CHE/2013

(51) Int. Cl.
C07D 487/00 (2006.01)
C07D 487/04 (2006.01)
A61K 31/519 (2006.01)

(52) U.S. Cl.
CPC .......... *C07D 487/04* (2013.01); *A61K 31/519* (2013.01)

(58) Field of Classification Search
CPC .................................................. C07D 487/04
USPC ....................................................... 544/280
See application file for complete search history.

(56) References Cited

U.S. PATENT DOCUMENTS

| | | | |
|---|---|---|---|
| 2010/0305319 A1 | 12/2010 | Luo et al. | |
| 2015/0259348 A1* | 9/2015 | Sharawat | C07D 487/04 514/265.1 |

FOREIGN PATENT DOCUMENTS

| | | |
|---|---|---|
| CN | 1778797 T | 5/2006 |
| EP | 0432677 A1 | 6/1991 |
| EP | 0549886 A1 | 7/1993 |
| EP | 0589720 A2 | 3/1994 |
| EP | 2213674 A1 | 8/2010 |
| IN | 4322/CHE/2012 A | 3/2013 |
| IN | 4422/CHE/2012 A | 3/2013 |
| IN | 4547/CHE/2012 A | 3/2013 |
| WO | 99/016742 A1 | 4/1999 |
| WO | 2000/011004 A1 | 3/2000 |
| WO | 2001/014379 A2 | 3/2001 |

* cited by examiner

*Primary Examiner* — Jeffrey H Murray

(57) ABSTRACT

The present invention provides process for preparing crystalline Pemetrexed dipotassium (I) Form-SP9

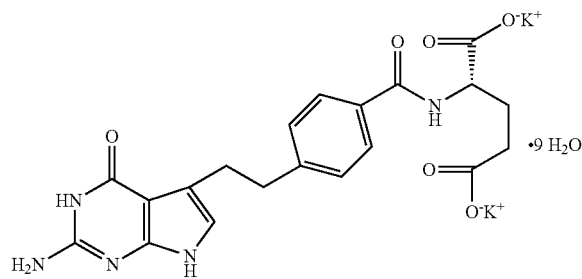

characterized by X-ray powder diffraction pattern comprising at least 5 characteristic 2θ° peaks selected from the XRPD peak set of 5.0, 12.5, 17.2, 20.8, 22.4, 25.7, 26.9 and 27.9±0.2 2θ°. The invention also provides process for preparing its pharmaceutical composition thereof, which may be useful for anti-cancer treatment.

9 Claims, 2 Drawing Sheets

PROCESS FOR CRYSTALLINE PEMETREXED DIPOTASSIUM SALT

FIELD OF THE INVENTION

The present invention relates to Crystalline Pemetrexed dipotassium (I) Form-SP9 characterized by X-ray powder

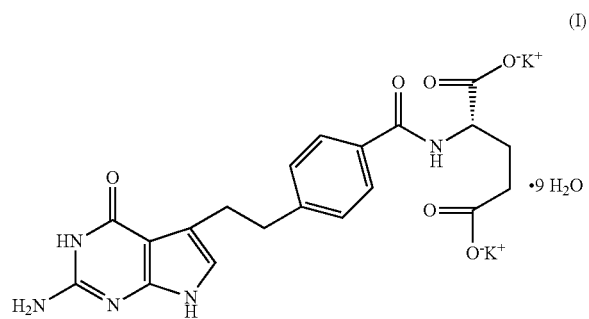

BACKGROUND OF THE INVENTION

Pemetrexed's chemical name is (S)-2-(4(2-(2-(2-amino-4-oxo-4,7-dihydro-3H-pyrrolo[2,3-d]pyrimidin-5-yl)ethyl)benzamido)pentanedioic acid and has the following chemical structure:

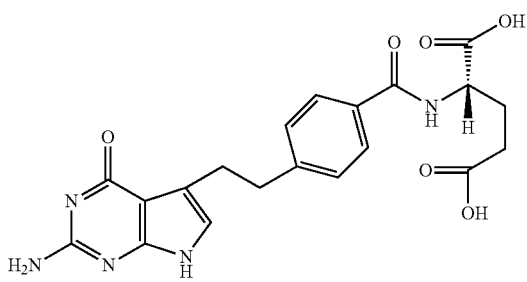

Pemetrexed disodium is the most common salt of pemetrexed di acid. It has the chemical name L-Glutamic acid, N-[4-[2-(2-amino-4,7-dihydro-4-oxo-1H-pyrrolo[2,3-d]pyrimidin-5-yl)-ethyl]benzoyl]-, disodium salt. Pemetrexed disodium heptahydrate is the active ingredient of Eli Lilly and Company's ALIMTA® injectable composition. Pemetrexed disodium heptahydrate has the following chemical structure:

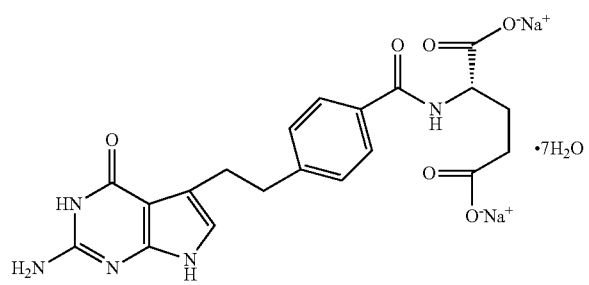

Pemetrexed disodium is a multi-targeted antifolate that strongly inhibits various folate-dependent enzymes, including Thymidylate Synthase (TS), DiHydroFolate Reductase (DHFR) and GlycinAmide Ribonucleotide Formyl Transferase (GARFT). Currently, Pemetrexed disodium is commercial available in USA, European Union, Canada, Japan and China etc. for treatment of malignant pleural stromal tumor as a first-line drug, and local advanced and metastatic non-small cell lung cancer as a second-line drug. In the treatment of malignant pleural stromal tumor, Pemetrexed disodium is a unique chemotherapeutic agent in the market currently. In the second-line treatment of non-small cell lung cancer, Pemetrexed disodium has a comparative efficacy and reduced toxicities compared with the standard drug Docetaxel. Hence, it is likely for Pemetrexed disodium to become a new standard treatment of the second-line treatment for non-small cell lung cancer. In addition, the clinical studies of Pemetrexed disodium in the treatment of breast, bowel, pancreatic, head and neck, gastric and bladder cancers are still ongoing.

Various methods for preparing Pemetrexed and Pemetrexed disodium are disclosed in the art, such as WO2001014379A, WO1999016742, EP432677, EP589720, WO0011004, EP549886 and CN1778797. Luo Jie et al in U.S.20100305319A1 (equivalent: EP 2213674B1) describes a method of purifying a salt of pemetrexed have a structure of formula (III)

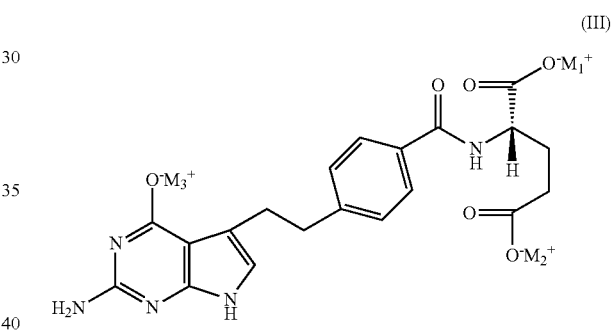

by salting-out, wherein if $M_3^+$ is $H^+$, then each of $M_1^+$ and $M_2^+$ is independently $H^+$, $Li^+$, $Na^+$ or $K^+$, provided that both of them are not $H^+$; if $M_3^+$ is $Li^+$, $Na^+$ or $K^+$, then each of $M_1^+$ and $M_2^+$ is independently $Li^+$, $Na^+$ or $K^+$. In example 16 and 17, it provides mention of purification of potassium pemetrexed, however, it appears that it does not refer to anything other than mono potassium salt of pemetrexed with no characterization details of the said salt. Further, in our attempt to reproduce the said example's disclosure, no material could be recovered.

First authentic disclosure of Pemetrexed Dipotassium salt, its polymorphic forms and formulations thereof is found in Indian published patent application Nos. 4322/CHE/2012, 4422/CHE/2012 and 4547/CHE/2012.

Pemetrexed being an important anticancer therapeutic agent, additional and improved ways of preparing Pemetrexed pharmaceutically acceptable salts and their polymorphs may be of immense value to pharmaceutical science and the healthcare of cancer patients.

Existence of polymorphism is known to be unique phenomenon in solid materials, wherein existence of different physical forms including shape, size, and arrangement of molecules in the physical state or polymorphs of same compound are known in the nature. A single compound, or a salt complex, may give rise to a variety of solids having distinct physical properties, which often results in substantial differences in bioavailability, stability, and other differences between production lots of formulated pharmaceutical products. Due to this reason, since polymorphic forms can vary in their chemical and physical properties, regulatory authorities often require that efforts be made to identify all forms, e.g., hydrate or anhydrate, crystalline or amorphous, solvated or un-solvated forms, etc. of the drug substances.

Some of the new polymorphic forms may turn out to be more efficacious than the other already reported forms. It has generally been observed that some forms of a compound have improved physical and chemical properties without affecting the pharmacological action of the drug and hence provide an opportunity to improve the drug performance characteristics of such product. However, the existence, and possible number, of polymorphic forms for a given compound cannot be predicted. In addition, there are no "standard" procedures that can be used to prepare different polymorphic forms of a substance.

Hence, there exists a need for the development of new stable crystalline forms and economically viable processes for preparation of Pemetrexed dipotassium, which shall be viable, industrially amenable to scale up, safer for handling, less time consuming and with better and consistent quality parameters.

The inventors of this application have found a new form of Pemetrexed i.e. Pemetrexed dipotassium (I) designated as Form-SP9, which is stable and free from any contamination.

Inventors of this application also provide a process for preparation of the said Pemetrexed dipotassium (I) Form-SP9.

SUMMARY OF INVENTION

Particular aspects of the present application relate to the crystalline Pemetrexed dipotassium (I) Form-SP9

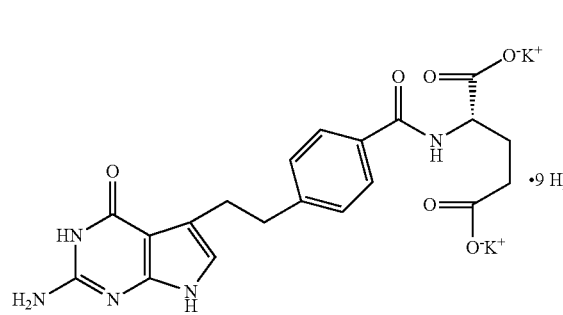

(I)

·9 H$_2$O and process/es for preparation thereof.

Individual aspects of the application relate to stable crystalline Pemetrexed dipotassium (I) Form-SP9, substantially free from process related impurities and process for preparation thereof. The crystalline polymorphic Form-SP9 of Pemetrexed dipotassium (I) obtained by the processes according to the present invention is useful as active pharmaceutical ingredient in pharmaceutical compositions for treating hyper-proliferative disorders, such as cancer, by administering the compound in a composition. Different aspects of the present application are summarized herein below individually.

In one aspect of the present application, it relates to crystalline Pemetrexed dipotassium (I) Form-SP9. Crystalline Form-SP9 of Pemetrexed dipotassium is characterized by X-ray powder diffraction pattern comprising at least 5 characteristic 2θ° peaks selected from the XRPD peak set of 5.0, 12.5, 17.2, 20.8, 22.4, 25.7, 26.9 and 27.9±0.2 2θ°. A few further characterizing XRPD diffraction angle peaks include 12.8, 14.8, 15.7, 24.1, 24.6 and 28.2±0.2 2θ°.

Crystalline Pemetrexed dipotassium (I) Form-SP9 of the present invention is characterized by X-ray powder diffraction pattern substantially according to FIG.-1 and DSC isotherm comprising at least one endotheimic peak ranging between—65 to 82° C. (Peak-1) or 85 to 100° C. (Peak-2). Crystalline Pemetrexed dipotassium (I) Form-SP9 is further characterized by HPLC purity greater than 99.8%, water content in the range between 23.0 to 25.5% w/w or residual solvents below limit of detection.

In yet another aspect of the present invention, it relates to a process for preparing crystalline Pemetrexed dipotassium (I) Form-SP9 characterized by X-ray powder diffraction pattern comprising at least 5 characteristic 2θ° peaks selected from the XRPD peak set of 5.0, 12.5, 17.2, 20.8, 22.4, 25.7, 26.9 and 27.9±0.2 2θ°, comprising the steps of—
 a. providing a solution of Pemetrexed dipotassium in water;
 b. cooling the reaction mixture to temperature below 10° C.;
 c. addition of a polar organic solvent to the reaction to obtain a reaction mass;
 d. treating the reaction mass with a secondary solvent;
 e. isolating the crystalline material Pemetrexed dipotassium (I) Form-SP9.

In yet another aspect, the crystalline Pemetrexed dipotassium (I) Form-SP9 obtained by the process/es of the present application may be formulated as solid compositions in the form of lyophilized powder, capsules, tablets, pills, powders or granules useful in the treatment of hyper-proliferative disorders, such as cancer.

Further aspects of the present invention are demonstrated in detailed description section as well as examples.

ABBREVIATIONS

DHFR Dihydro Folate Reductase
DM water De-Mineralized Water
DSC Differential Scanning Calorimetry
GARFT Glycin Amide Ribonucleotide Formyl Transferase
HPLC High-Performance Liquid Chromatography
KF Karl Fischer
RB Flask Round-Bottom Flask
TGA Thermo-Gravimetric Analysis
TS Thymidylate Synthase
XRPD X-Ray Powder Diffraction Pattern

DETAILED DESCRIPTION

As set forth herein, embodiments of the present invention provide crystalline Pemetrexed dipotassium (I) Form-SP9 and processes for preparation thereof. Individual embodiments of the present invention are detailed herein below separately.

In one embodiment of the present application, it provides crystalline Pemetrexed dipotassium (I) Form-SP9.

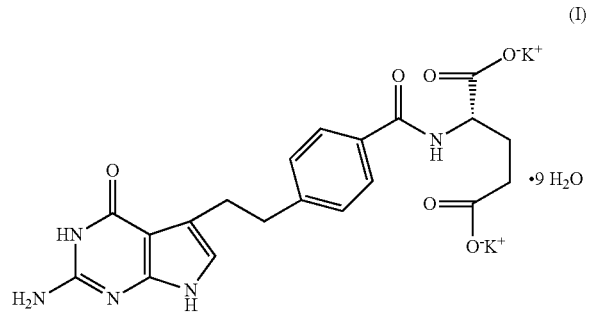

(I)

Crystalline Form-SP9 of Pemetrexed dipotassium is characterized by X-ray powder diffraction pattern comprising at least 5 characteristic 2θ° peaks selected from the XRPD peak set of 5.0, 12.5, 17.2, 20.8, 22.4, 25.7, 26.9 and 27.9±0.2 2θ°. A few further characterizing XRPD diffraction angle peaks include 12.8, 14.8, 15.7, 24.1, 24.6 and 28.2±0.2 2θ°.

Figure 1:
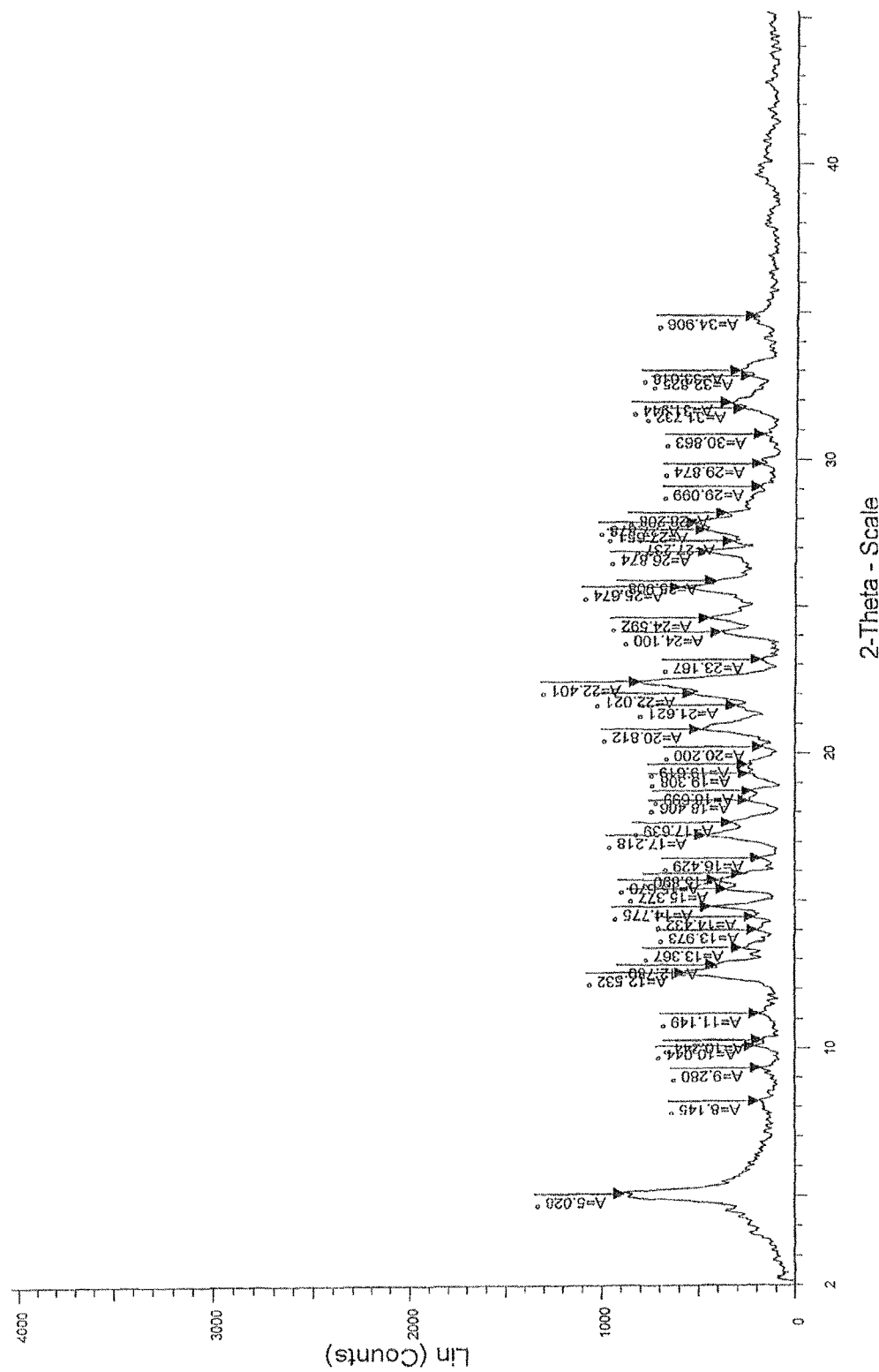
FIG. 1 is Illustration of X-ray powder diffraction (XRPD) pattern of Crystalline Pemetrexed dipotassium (I) Form-SP9.
Figure 2:
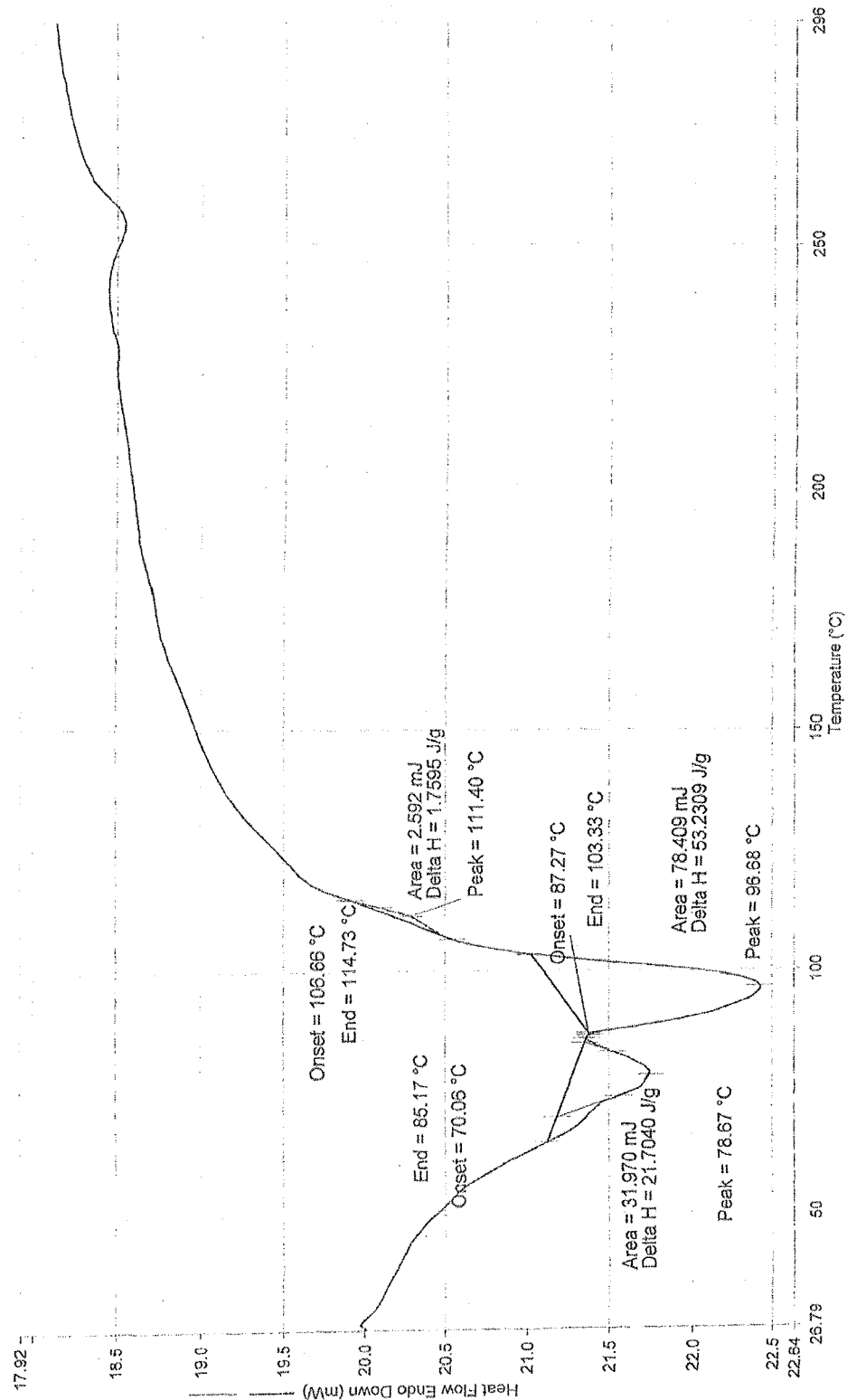
FIG. 2 is Illustration of Differential Scanning Calorimetry ("DSC") curve of Crystalline Pemetrexed dipotassium (I) Form-SP9.

Crystalline Pemetrexed dipotassium (I) Form-SP9 is further characterized by X-ray powder diffraction pattern substantially according to FIG.-1 and DSC isotherm comprising at least one endothermic peak ranging between—65 to 82° C. (Peak-1) or 85 to 100° C. (Peak-2). The characteristic X-ray powder diffraction peaks and corresponding d-spacing values of the novel Crystalline Pemetrexed dipotassium (I) Form-SP9 for a particular batch material are tabulated in the Table-1.

TABLE-1

Characteristic XRPD Peaks of Crystalline Pemetrexed dipotassium (I) Form-SP9

| S. No. | Angle (2θ°) ± 0.20 | d-Spacing Value (A°) |
|---|---|---|
| 1. | 5.02 | 17.559 |
| 2. | 12.53 | 7.057 |
| 3. | 12.78 | 6.921 |
| 4. | 14.77 | 5.990 |
| 5. | 15.67 | 5.650 |
| 6. | 17.22 | 5.145 |
| 7. | 20.81 | 4.264 |
| 8. | 22.40 | 3.965 |
| 9. | 24.10 | 3.689 |
| 10. | 24.59 | 3.617 |
| 11. | 25.67 | 3.467 |
| 12. | 26.87 | 3.314 |
| 13. | 27.88 | 3.197 |
| 14. | 28.21 | 3.161 |

Minor variations in the observed 2θ° angles values may be expected based on the analyst, the specific XRPD diffractometer employed and the sample preparation technique. Further possible variations may also be expected for the relative peak intensities, which may be largely affected by the non-uniformity of the particle size of the sample. Hence, identification of the exact crystalline form of a compound should be based primarily on observed 2θ angles with lesser importance attributed to relative peak intensities. The 2θ diffraction angles and corresponding d-spacing values account for positions of various peaks in the X-ray powder diffraction pattern. D-spacing values are calculated with observed 2θ angles and copper Kα wavelength using the Bragg equation well known to those of having skill in the art of XRPD diffractometry science.

In view of possibility of marginal error in the assigning 2θ angles and d-spacing, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified crystalline form of Pemetrexed dipotassium over FIG. 1 and readily determine whether the X-ray diffraction pattern of the unidentified form is substantially the same as the X-ray powder diffraction pattern of the crystalline form of this invention. If the X-ray powder diffraction pattern is substantially the same as FIG. 1, the previously unknown crystalline form of Pemetrexed dipotassium can be readily and accurately identified as the crystalline Form-SP9 of this invention.

The crystalline Form-SP9 of Pemetrexed dipotassium is a nonahydrate form, which is evident from the moisture content results. A sample of the crystalline Form-SP9 prepared by the inventors of this application showed moisture content up to about 24.78% w/w by KF method, which confirms the nonahydrate nature of the compound (theoretical water content as calculated—24.34% w/w). While the invention is not limited to any specific theory, it should be understood however that the crystalline Form-SP9 of Pemetrexed dipotassium may contain additional residual or unbound moisture without losing its character and/or its crystalline Form-SP9 characteristics. Nevertheless, person having skill in the art should be able to determine whether they are same crystalline forms or not, by looking at the overall shape of the X-ray powder diffraction pattern optionally with help of other thermal data like DSC or TGA.

In yet another embodiment of the present invention, it provide process for preparing crystalline Pemetrexed dipotassium (I) Form-SP9 characterized by X-ray powder diffraction pattern comprising at least 5 characteristic 2θ° peaks selected from the XRPD peak set of 5.0, 12.5, 17.2, 20.8, 22.4, 25.7, 26.9 and 27.9±0.2 2θ°, comprising the steps of—
a. providing a solution of Pemetrexed dipotassium in water;
b. cooling the reaction mixture to temperature below 10° C.;
c. addition of a polar organic solvent to the reaction to obtain a reaction mass;
d. treating the reaction mass with a secondary solvent;
e. isolating the crystalline material Pemetrexed dipotassium (I) Form-SP9.

The individual steps of the process according to the present invention for preparing crystalline Pemetrexed dipotassium (I) Form-SP9 are detailed separately herein below.

Step a) comprises providing a solution of Pemetrexed dipotassium in water;

Pemetrexed dipotassium salt obtained from any source or having any grade of purity or having any polymorphic form (other than Form-SP9) is provided as solution in water. Amount of water used in this step ranges from 2-6 times v/w (mL/g) w.r.t. the amount of Pemetrexed dipotassium taken. The solution is prepared at room temperature, though slight heating may also be performed as per requirement. The reaction mixture is stirred for time ranging from 15 minutes to 1 hr to obtain a clear solution. The solution obtained is then filtered by using conventional methods known in the prior art for e.g. by use of micron filter paper. The filtrate obtained is then transferred to another reaction set-up.

Step b) comprises cooling the reaction mixture to temperature below 10° C.;

The reaction mixture (filtrate) obtained from step a) is subjected to cooling to a temperature below 10° C. In a preferred embodiment the reaction mixture is cooled to a temperature of 0-5° C. Cooling shall be performed in a controlled manner wherein rate of cooling from room temperature to a temperature below 10° C. shall not exceed 1° C. per minute. Throughout the cooling process, reaction mixture is maintained in the state of continuous stirring.

Step c) comprises addition of a polar organic solvent to the reaction to obtain a reaction mass;

To the cooled reaction mixture obtained from step b) a polar organic solvent is added. Polar organic solvent used in this reaction is preferably a (C1 to C5) alcohol wherein (C1 to C5) alcohol may be selected from methanol, ethanol, n-propanol, isopropanol, n-butanol, amyl alcohol or isoamyl alcohol.

The amount of polar organic solvent used in this reaction step ranges from 10-20 times v/w (mL/g) w.r.t. the amount of Pemetrexed dipotassium taken initially at the start of the reaction. Care is to be taken that addition of polar organic solvent into the reaction mixture is carried out in a drop-wise manner, which is necessary to comply with the optimum end-product characteristics, like favorable impurity profile. In a specific embodiment of the present invention 420 mL of polar organic solvent i.e. ethanol, was added to the reaction mixture obtained from step b), in 45 mins. Addition of polar organic solvent to the reaction mixture is carried out at low temperature of below 10° C. and under continuous stirring. The stirring of reaction mixture may be carried out for time ranging from 2-5 hrs, while maintaining the low temperature conditions.

The compound obtained after stirring is subjected to filtration, suck drying, and washing with polar organic solvent as described above (same or different w.r.t. the polar organic solvent added initially) followed by further drying to obtain a wet solid mass.

Step d) comprises treating the reaction mass with a secondary solvent;

Wet solid mass obtained from step c) is added to a reaction set up containing secondary solvent selected from a (C3-C6) ketone solvent like acetone, butanone or pentanone. Amount of secondary solvent used in this step varies from 3-10 times v/w (mL/g) w.r.t. the amount of Pemetrexed dipotassium taken initially at the start of the reaction. This reaction step is carried out at ambient temperature of 25-35° C. under continuous stirring which may be carried out for time ranging from 30 mins to 2 hrs. After completion of stirring, the compound obtained is filtered using any conventional procedure known to person having skill in the art. The solid material is then optionally again given washing with a secondary solvent as described above.

Step e) comprises isolating the crystalline material Pemetrexed dipotassium (I) Form-SP9. The wet solid material obtained from step d) is sufficiently suck dried for time ranging between 5 mins to 30 mins. If required low pressure conditions like vacuum may also be utilized for the drying procedure. The dried crystalline solid material is directly obtained as Pemetrexed dipotassium (I) Form-SP9 which is characterized by HPLC purity greater than 99.8%, water content in the range between 23.0 to 25.5% w/w and residual solvents below limit of detection.

The isolation of product from the reaction mass may involve additional conventional processes including filtering and further drying, which may be carried out at room temperature for the suitable durations to retain the crystalline polymorphic form characteristics. Crystalline Form-SP9 can be recovered by conventional processes, which are not limited to scrapping, breaking, and triturating.

Crystalline Form-SP9 is found to be a very stable crystal lattice which is adequately stable to handle and store for longer time without any significant or measurable change in its morphology and physicochemical characteristics. Crystalline Form-SP9 retains its stoichiometry even on exposure to uncontrolled environmental conditions. This stable form thus, offers various advantages in terms of storage, shelf life and favorable impurity profile.

Any form of Crude or Pure Pemetrexed dipotassium salt obtained by any process may be used for preparing Form-SP9. Crystalline Pemetrexed dipotassium (I) Form-SP9 of the present invention may have one or more advantageous and desirable properties compared to the known Crystalline Pemetrexed disodium salt, which are not limited to better stability, low hygroscopicity, high solubility and high purity leading to improved storage and distribution.

The process related impurities, including degradation products and other medium dependent impurities like residual solvent, that appear in the impurity profile of the Pemetrexed dipotassium can be substantially removed by the process of the present invention resulting in the formation pure crystalline Form-SP9. A substantially pure product i.e. Pemetrexed dipotassium (I) Form-SP9 having purity more than 99.8% (by HPLC) can be obtained in high yield by the process of the present invention.

The crystalline Pemetrexed dipotassium (I) Form-SP9 described herein may be characterized by X-ray powder diffraction pattern (XRPD) and IR absorption spectra and Thermal techniques such as differential scanning calorimetric (DSC) Analysis and TGA. The samples of Crystalline Pemetrexed dipotassium (I) Form-SP9 were analyzed by XRPD on a Bruker AXS D8 Advance Diffractometer using X-ray source—Cu Kα radiation using the wavelength 1.5418 Å. DSC was done on a Perkin Elmer Pyris 7.0 instrument. Illustrative example of analytical data for the Crystalline Pemetrexed dipotassium (I) Form-SP9 obtained in the Examples is set forth in the FIG. 1.

In a further embodiment, present invention provides that the Crystalline Pemetrexed dipotassium (I) Form-SP9 obtained by the process(es) of the present application may be formulated as lyophilized powder composition as injectable or solid compositions for oral administration in the form of capsules, tablets, pills, powders or granules useful in the treatment of hyper-proliferative disorders, such as cancer. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin.

The compositions for parenteral administration can be lyophilized powder, suspensions, emulsions or aqueous or non-aqueous sterile solutions. In other compositions, as a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising Crystalline Pemetrexed dipotassium (I) Form-SP9 of the present application include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from Crystalline Pemetrexed dipotassium (I) Form-SP9 of the present application may also comprise to include the pharmaceutically acceptable carrier(s) used for the preparation of solid dispersion, wherever utilized in the desired dosage form preparation.

Certain specific aspects and embodiments of the present application will be explained in more detail with reference to the following examples, which are provided by way of illustration only and should not be construed as limiting the scope of the invention in any manner.

Experimental Details

The preparation of Crystalline Pemetrexed dipotassium (I) Form-SP9 according to process of the present invention may be demonstrated by examples as given below.

Example-1: Preparation of Crystalline Pemetrexed Dipotassium (I) Form-SP9

120 mL of DM water was charged in to a 1 L RB flask at room temperature and under stirring 30 g Pemetrexed Dipotassium was added to it. The reaction mixture was stirred for 15 minutes to obtain a clear solution, which was then filtered through a micron filter paper. The filtrate obtained was then charged into another RB flask and under continuous stirring it was cooled to ~5° C.

To the cooled reaction mixture 420 mL of ethanol was added drop-wise within 45 mins, while continuing the stirring. At the same low temperature the reaction mass was stirred for 3.5 hrs. From the reaction mass obtained, the compound was filtered and suck dried for 10 minutes. The partially dried solid material was then washed with 60 mL of ethanol. The solid material was then suck dried for 30 minutes and the obtained partially wet compound was loaded into another RB flask followed by addition of 150 mL acetone. The reaction mass was stirred for 1 hr at ~30° C. Then the compound obtained was filtered, washed with 30 mL acetone, suck dried for 5 minutes and unloaded to obtain the title compound.

Yield: 23.0 g, 76.66%
HPLC purity: 99.84%
Water content (by KF): 25.13% w/w

Example-2: Preparation of Crystalline Pemetrexed Dipotassium (I) Form-SP9

125 mL of DM water was charged in to a 1 L RB flask at room temperature and under stirring 31 g Pemetrexed Dipotassium was added to it. The reaction mixture was stirred for 20 minutes to obtain a clear solution, which was then filtered through a micron filter paper. The filtrate obtained was then charged into another RB flask and under continuous stirring it was cooled to ~0° C.

To the cooled reaction mixture 430 mL of ethanol was added drop-wise within 60 mins, while continuing the stirring. At the same low temperature the reaction mass was stirred for 4 hrs. From the reaction mass obtained, the compound was filtered and suck dried for ~10 minutes. The partially dried solid material was then washed with 65 mL of ethanol. The solid material was then suck dried for ~30 minutes and the obtained partially wet compound was loaded into another RB flask followed by addition of 160 mL acetone. The reaction mass was stirred for 1 hr at ~25° C. Then the compound obtained was filtered, washed with 35 mL acetone, suck dried for ~10 minutes and unloaded to obtain the title compound.

Yield: 23.5 g, 76.66%
HPLC purity: 99.91%
Water content (by KF): 24.78% w/w

The abovementioned examples, which are provided by way of illustration, should not be construed as limiting the scope of the invention with respect to parameter/s, ingredient/s and quantities used in any manner.

Literature, references, including publications, issued patents and patent applications, cited in the specification are hereby incorporated by reference to the same extent as if each reference were individually and specifically indicated to be incorporated by reference and were set forth in its entirety herein.

Usage of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The term wt % refers to percent by weight. All methods described herein can be performed in any suitable order unless otherwise indicated herein or otherwise clearly contradicted by context. The use of any and all examples or exemplary language (e.g. "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. Crystalline Pemetrexed dipotassium (I) Form-SP9 characterized by X-ray Powder

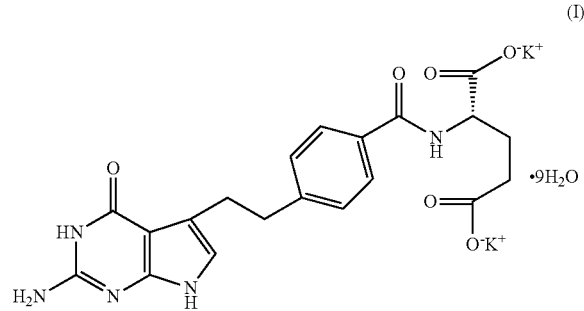

(I)

diffraction pattern comprising at least 5 characteristic 2θ° diffraction angle peaks selected from the XRPD peak set of 5.0, 12.5, 17.2, 20.8, 22.4, 25.7, 26.9 and 27.9±0.2 2θ°.

2. Crystalline Pemetrexed dipotassium (I) Form-SP9 according to claim 1, further characterized by XRPD diffraction angles at 12.8, 14.8, 15.7, 24.1, 24.6 and 28.2±0.2 2θ°.

3. Crystalline Pemetrexed dipotassium (I) Form-SP9 according to claim 1, characterized by water content (by KF) in the range between 23.0 to 25.5 w/w.

4. Crystalline Pemetrexed dipotassium (I) Form-SP9 according to claim 1, characterized by X-ray powder diffraction pattern substantially according to Fig-I and DSC isotherm comprising at least one endothermic peak ranging between
   a) Peak-1—Between 65 to 82° C.; or
   b) Peak-2—Between 85 to 100° C.

5. A process for preparing crystalline Pemetrexed dipotassium (I) Form-SP9 characterized by X-ray powder diffraction pattern comprising at least 5 characteristic 2θ° peaks selected from the XRPD peak set of 5.0, 12.5, 17.2, 20.8, 22.4, 25.7, 26.9 and 27.9±0.2 2θ°, comprising the steps of
   a) providing a solution of Pemetrexed dipotassium in water;
   b) cooling the reaction mixture to temperature below 10° C.;
   c) addition of a polar organic solvent to the reaction to obtain a reaction mass;
   d) treating the reaction mass with a secondary solvent;
   e) isolating the crystalline material Pemetrexed dipotassium (I) Form-SP9.

6. A process for preparing crystalline Pemetrexed dipotassium (I) Form-SP9 according to claim 5, wherein polar organic solvent is selected from (CI to C5) alcohol selected from methanol, ethanol, n-propanol, isopropanol, n-butanol, amyl alcohol or isoamyl alcohol.

7. A process for preparing crystalline Pemetrexed dipotassium (I) Form-SP9 according to claim 5, wherein secondary solvent is a (C3-C6) ketone solvent, selected from acetone, butanone or pentanone.

8. Crystalline Pemetrexed dipotassium (I) Form-SP9 according to claim 1, wherein the Form-SP9 is characterized by HPLC purity greater than 99.8%, water content in the range between 23.0 to 25.5% w/w or residual solvents below limit of detection.

9. A pharmaceutical composition comprising crystalline Pemetrexed dipotassium (I) Form-SP9 and at least one pharmaceutically acceptable excipient, diluent, or carrier.

* * * * *